United States Patent [19]

Alig et al.

[11] Patent Number: 4,892,886

[45] Date of Patent: Jan. 9, 1990

[54] PHENOXYPROPANOLAMINES

[75] Inventors: Leo Alig, Kaiseraugst; Marcel Müller, Frenkendorf, both of Switzerland

[73] Assignee: Hoffman-La Roche Inc., Nutley, N.J.

[21] Appl. No.: 350,056

[22] Filed: May 10, 1989

Related U.S. Application Data

[63] Continuation of Ser. No. 215,195, Jul. 5, 1988, abandoned.

[51] Int. Cl.⁴ .................................... A61K 31/195
[52] U.S. Cl. ............................ 514/567; 562/452; 560/42; 514/539; 514/866; 514/909
[58] Field of Search .............. 514/567, 539, 806, 909; 560/42; 502/452

[56] References Cited

U.S. PATENT DOCUMENTS

| | | | |
|---|---|---|---|
| 3,723,476 | 3/1973 | Nakanishi et al. | 514/567 |
| 3,723,524 | 3/1973 | Augstein et al. | 514/567 |
| 3,892,799 | 7/1975 | Pinhas | 562/452 |
| 4,161,542 | 7/1979 | Carlsson et al. | 514/567 |
| 4,165,384 | 8/1979 | Carlsson et al. | 560/42 |
| 4,171,370 | 10/1979 | Jonas et al. | 562/452 |
| 4,252,984 | 2/1981 | Manoury et al. | 562/452 |
| 4,263,325 | 4/1981 | Carlsson et al. | 560/42 |
| 4,338,333 | 7/1982 | Ainsworth et al. | 514/567 |
| 4,338,338 | 7/1982 | Ainsworth et al. | 514/567 |
| 4,382,958 | 5/1983 | Duckworth | 562/452 |
| 4,395,391 | 7/1982 | Pfeiffer et al. | 562/452 |
| 4,450,173 | 5/1984 | Erhardt et al. | 562/452 |
| 4,629,737 | 12/1986 | Cantello | 514/507 |
| 4,753,962 | 6/1988 | Ainsworth et al. | 514/538 |
| 4,772,631 | 9/1988 | Holloway et al. | 514/567 |

FOREIGN PATENT DOCUMENTS

| | | | |
|---|---|---|---|
| 140243 | 10/1984 | European Pat. Off. | 514/567 |
| 0170121 | 7/1985 | European Pat. Off. | 514/567 |
| 2503222 | 7/1976 | Fed. Rep. of Germany | 514/567 |

*Primary Examiner*—James H. Reamer
*Attorney, Agent, or Firm*—George M. Gould; Bernard S. Leon; William G. Isgro

[57] ABSTRACT

[p-[2-[[(S)-2-hydroxy-3-phenoxypropyl]amino]-ethyl]-phenoxy]acetic acid and its physiologically compatible salts, which have catabolic activity and can be used for the treatment of obesity, of diabetes and of conditions which are associated with increased protein breakdown or as feed additives for fattening animals, as described. The compounds are prepared starting from esters corresponding to the aforementioned acid.

5 Claims, No Drawings

PHENOXYPROPANOLAMINES

This is a continuation division of application Ser. No. 07/215,195 filed July 5, 1988 now abandoned.

BRIEF DESCRIPTION OF THE INVENTION

The invention relates to phenoxypropanolamines, a process for their preparation and pharmaceutical compositions based on the referred to compounds, as well as the use of the compounds in the control or prevention of illnesses.

The phenoxypropanolamines are [p-[2-[[(S)-2-hydroxy-3-phenoxypropyl]amino]ethyl]phenoxy]acetic acid (referred to hereinafter a HPA) and its physiologically compatible salts.

DETAILED DESCRIPTION OF THE INVENTION

The invention relates to phenoxypropanolamines, a process for their preparation and pharmaceutical compositions based on the referred to compounds, as well as the use of the compounds in the control or prevention of illnesses.

The phenoxypropanolamines are [p-[2-[[(S)-2-hydroxy-3-phenoxypropyl]amino]ethyl]phenoxy]acetic acid (referred to hereinafter a HPA) and its physiologically compatible or pharmaceutically acceptable salts. Examples of such salts are alkali metal, alkaline earth metal, ammonium and alkylammonium salts, such as, Na, K, Ca, trimethylammonium and ethanolammonium salts as well as salts of HPA with mineral acids, such as, hydrochloric acid, hydrobromic acid, sulfuric acid or phosphoric acid or with organic acids, such as, oxalic acid, methanesulfonic acid, acetic acid, propionic acid, citric acid, maleic acid, succinic acid, malic acid fumaric acid phenylacetic acid or salicylic acid. HPA hydrochloride is preferred.

The phenoxypropanolamines can be prepared by cleaving an ester corresponding to the [p-[2-[[(S)-2-hydroxy-3-phenoxypropyl]amino]ethyl]phenoxy]acetic acid and, if desired, converting the acid obtained into a salt.

As esters there come into consideration for example, lower-alkyl esters or the benzyl ester of HPA. The lower-alkyl esters can be cleaved by saponification under acidic or basic conditions for example, with a strong acid, such as, hydrochloric acid, sulfuric acid or phosphoric acid, conveniently at a temperature between 20° and 110° C., in a polar solvent, such as, water, a $C_{1-4}$-alkanol, for example, methanol or ethanol; or with a base, such as, sodium or potassium hydroxide, conveniently at a temperature between 10° and 110° in a suitable solvent, such as, a $C_{1-4}$-alkanol. The benzyl ester of HPA can be cleaved by catalytic hydrogenation. Conveniently, the HPA can be isolated from the reaction mixture in the form of a salt. The free HPA can be isolated by extraction from the aqueous reaction medium with an organic solvent, such as, methylene chloride or chloroform, at pH 6 to 7.

The ester starting material can be prepared in a known manner, for example, starting from (S)-phenyl glycidyl ether and tyramine via p-[2-[[(S)-2-hydroxy-3-phenoxypropyl]amino]ethyl]phenol and reacting this phenol with a lower alkyl haloacetate, such as, methyl bromoacetate. The latter reaction can be carried out for example, in a solvent, such as, dimethyl sulfoxide in the presence of a base, such as, potassium t-butylate at a temperature up to the reflux temperature of the reaction mixture. Alternatively, the ester starting material can be prepared by reacting (S)-phenyl glycidyl ether with a lower-alkyl p-[2-aminoethyl]phenoxyacetate.

The compounds in accordance with the invention can be used as active substances in pharmaceutical preparations for the treatment of obesity and/or of diabetes mellitus, especially of obese adult diabetics. In an animal experiment, an increased catabolism, primarily of fat, has been observed upon the administration of the compounds of the invention. Furthermore, it has been observed that the compounds of the invention stimulate the formation of brown adipose tissue in rats and obese-hyperglycemic mice. It is known that defects of the brown adipose tissue play a substantial role in the origin of obesity. In obese-hyperglycemic mice and in streptozotocin-diabetic rats, the compounds of the invention have a pronounced anti-diabetic effect, that is, they have hypoglycemic activity and reduce glycosuria. The compounds of the invention exhibit only a slight activity on the working of the heart and circulation. The dosage can amount to 0.5-1000 mg, preferably 2-200 mg, per day for an adult depending on the strength of activity of the individual compounds and on the individual requirements of the patients, whereby the dosage can be administered as a single dose or in several divided doses over the day.

In addition, in an animal experiment utilizing the compounds of the invention, an increase in the protein content of the body and a decrease in the fat content of the body could be detected. The compounds in accordance with the invention therefore lead to an increase in the lean composition of the body at the expense of fat. Accordingly, the compounds of the invention can be used in human medicine for the treatment of conditions which are associated with an increased protein breakdown, for example, in convalescence after operations. In latter case, the dosages administered are the same as in the case of the treatment of obesity and/or diabetes mellitus.

The compounds of the invention can also be used in the maintenance of fattening animals, such as, beef cattle, pigs, sheep and poultry. In this case, the dosage administered and the dosage forms administered can be the same as in the case of vitamins. The compounds of the invention can also be used as feed additives in dosages of 0.01-100 mg/kg depending on the substance, kind of animal and age.

The pharmaceutical compositions contain the active substance together with a compatible pharmaceutical organic or inorganic carrier material, for example, water, gelatin, gum arabic, lactose, starch, magnesium stearate, talc, vegetable oils, polyalkylene glycols and the like. The pharmaceutical compositions are preferably administered orally, for example, in the form of tablets, capsules, pills, powders, granulates, solutions, syrups, suspensions, elixirs and the like. The administration can, however, also be carried out parenterally, for example, in the form of sterile solutions, suspensions or emulsions The pharmaceutical compositions can be sterilized and/or can contain ingredients, such as, preserving agents. stabilizers, wetting agents, emulsifiers, salts for varying the osmotic pressure and buffer substances.

The activity of the compounds of the invention is demonstrated and evident from the test results which follow:

ACTIVITY ON OXYGEN CONSUMPTION

Male albino rats weighing 160–180 g were placed in metabolic cages after fasting for 24 hours. The cages were ventilated with a constant 6 liters room air/minute which was equilibrated at a dew point of 11° C. Samples of the spent air were collected in each case during periods of 14 minutes after again equilibrating and the oxygen content and $CO_2$ content were analyzed. After an adaptation time of 4 hours, the animals, divided into groups of 6, received either placebo (5% gum arabic) or the test substance, namely HPA hydrochloride (suspended in 5% gum arabic), per oz. Thereafter, the determinations were carried out for a period of 12 hours. In the following Table there is given the percentage of the average oxygen consumption after medication during the first 3 hours and the entire test duration (12 hours) of the oxygen consumption of the adaptation period, corresponding corrections for variations in the placebo group having been taken into consideration.

TABLE

| Dosage ($\mu$M/kg) | Oxygen consumption (% of the value of the pre-period) | |
|---|---|---|
| | 1st to 3rd hour | 1st to 12th hour |
| 0.03 | 114 | 105 |
| 0.1 | 132 | 105 |
| 0.3 | 152 | 117 |
| 1 | 169 | 129 |

A slight chronotropic effect (tachycardia) occurred only in the case of the administration of about 100 $\mu$M/kg.

The following Examples illustrate further the invention.

EXAMPLE 1

1.90 g of methyl [p-[2-[[(S)-2-hydroxy-3-phenoxypropyl]amino]ethyl]phenoxy]acetate were heated to 50° C. for 90 minutes with 80 ml of 5% methanolic potassium hydroxide and 80 ml of water. The reaction solution was cooled, poured on to ice-water and extracted with ether. The aqueous-alkaline phase was acidified to pH 2 with concentrated hydrochloric acid and evaporated to dryness in a vacuum at 40° C. The residue was evaporated with toluene in a vacuum. The residue was triturated with 150 ml of a mixture of ethanol-methanol 2:1. The precipitate was removed by filtration and the filtrate was evaporated in a vacuum. The residue was dissolved in 20 ml of methanol and treated with 20 ml of ether, whereby 1.5 g of [p-[2-[[(S)-2-hydroxy-3-phenoxypropyl]amino]ethyl]phenoxy]acetic acid hydrochloride crystallized, melting point 194°–196° C. (dec.), $[\alpha]_D^{20°} = -18°$ (c=0.5 in methanol).

The starting material was prepared as follows: Reaction of S-phenyl glycidyl ether with tyramine gave p-[2-[[(S)-2-hydroxy-3-phenoxypropyl]amino]ethyl]phenol of m.p. 118°–119° C. This was reacted with methyl bromoacetate and potassium t-butylate in dimethylsulfoxide at room temperature to give amorphous methyl [p-[2-[[(S)-2-hydroxy-3-phenoxypropyl]amino]ethyl]phenoxy]acetate. This was crystallized from acetone as the hydrochloride of m.p. 167°–168° C., $[\alpha]_D^{20°} = -16°$ (c=1.0 in methanol).

EXAMPLE 2

382 mg of HPA hydrochloride were dissolved in 16 ml of ethanol and 4 ml of methanol and treated with 80 mg of sodium hydroxide. The solution was stored in a refrigerator for 1 hour, whereby there were obtained 270 mg of HPA sodium salt, melting point 200°–201° C., $[\alpha]_D^{20°} = -4.5°$ (c=0.5 in methanol).

EXAMPLE 3

382 mg of HPA hydrochloride were dissolved in 5 ml of hot methanol, treated with 40 mg of sodium hydroxide and cooled. The separated sodium chloride was removed by filtration and the filtrate was treated with 130 mg of maleic acid. 15 ml of ether were then added thereto and the mixture was left to crystallize in a refrigerator. There were obtained 300 mg of HPA maleate of melting point 163°–166° C., $[\alpha]_D^{20°} = -15°$ (c=0 6 in methanol).

EXAMPLE 4

Tablets of the following composition are prepared in the usual manner:

| | |
|---|---|
| [p-[2[[(S)-2-Hydroxy-3-phenoxypropyl]amino]ethyl]phenoxy]acetic acid hydrochloride | 250 mg |
| Lactose | 200 mg |
| Maize starch | 300 mg |
| Maize starch paste | 50 mg |
| Calcium stearate | 5 mg |
| Dicalcium phosphate | 45 mg |
| | 850 mg |

We claim:

1. [p-[2-[[(S)-2-Hydroxy-3-phenoxypropyl]amino]ethyl]phenoxy]acetic acid or a physiologically compatible salt thereof.

2. The compound in accordance with claim 1, [p-[2-[[(S)-2-Hydroxy-3-phenoxypropyl]amino]ethyl]phenoxy]acetic acid hydrochloride.

3. The compound in accordance with claim 1, (p-[2-[[(S)-2-hydroxy-3-phenoxypropyl]amino]ethyl]phenoxy]acetic acid.

4. A pharmaceutical composition comprising an effective amount of [p-[2-[[(S)-2-hydroxy-3-phenoxypropyl)amino]ethyl)phenoxy]acetic acid or a physiologically compatible salt thereof, and an inert carrier material.

5. A method of treating obesity, diabetes mellitus and conditions associated with an increased protein breakdown which comprises administering a therapeutically effective amount of [p-[2-[[(S)-2-hydroxy-3-phenoxypropyl]amino]ethyl]phenoxy]acetic acid or a physiologically compatible salt thereof.

* * * * *